US00RE39820E

(19) United States
(12) Reissued Patent
Banholzer et al.

(10) Patent Number: US RE39,820 E
(45) Date of Reissued Patent: Sep. 4, 2007

(54) ESTERS OF THIENYL CARBOXYLIC ACIDS AND AMINO ALCOHOLS AND THEIR QUATERNIZATION PRODUCTS

(75) Inventors: Rolf Banholzer, Stuttgart (DE); Rudolf Bauer, Ockenheim (DE); Richard Reichl, Gau-Algesheim (DE)

(73) Assignee: Boehringer Ingelheim Pharma GmbH & Co. KG, Ingelheim (DE)

(21) Appl. No.: 11/254,213

(22) Filed: Oct. 18, 2005

Related U.S. Patent Documents

Reissue of:
(64) Patent No.: 5,610,163
Issued: Mar. 11, 1997
Appl. No.: 08/405,111
Filed: Mar. 16, 1995

U.S. Applications:
(63) Continuation of application No. 08/254,324, filed on Jun. 6, 1994, now abandoned, which is a continuation of application No. 08/100,822, filed on Aug. 2, 1993, now abandoned, which is a continuation of application No. 07/838,724, filed on Mar. 13, 1992, now abandoned.

(30) Foreign Application Priority Data

Sep. 16, 1989 (DE) ..... 39 31 041.8
Sep. 8, 1990 (EP) ..... PCT/EP90/01517

(51) Int. Cl.
*A61K 31/435* (2006.01)
*C07D 451/12* (2006.01)

(52) U.S. Cl. ..... 514/291; 514/304; 546/18; 546/91; 546/125

(58) Field of Classification Search ..... 546/77, 546/18, 91, 125; 514/291, 304
See application file for complete search history.

(56) References Cited

U.S. PATENT DOCUMENTS

| | | | | |
|---|---|---|---|---|
| 3,673,195 A | | 6/1972 | Yoneda et al. | |
| 3,808,263 A | | 4/1974 | Yoneda | |
| 4,353,922 A | * | 10/1982 | Pfister | 514/339 |
| 4,855,422 A | | 8/1989 | Grimminger | |

FOREIGN PATENT DOCUMENTS

| | | | |
|---|---|---|---|
| DE | 1 166 787 | | 4/1964 |
| DE | 1166787 | * | 4/1964 |
| EP | 418716 | | 4/1994 |
| GB | 845056 | | 8/1960 |
| GB | 955535 | | 4/1964 |
| GB | 1350928 | | 4/1974 |

OTHER PUBLICATIONS

CAS Accession No. 1983:34827 (Pfister et al.).*
CAS Accession No. 1992:20937 (Banholzer et al.).*
Wilhelm, The Chemistry of Polycyclic Psycho–active Drugs: Serendipity or Systematic Investigation?, Pharm. J., 214:414–416 (1975).*
Frank & Maclaren, The Use of an Anticholinergic Drug in the treatment of Asthma, ANN. Allergy, 15(3):261–9 (1957).*
Nyberg et al., Investigations of Dithienylglycolic Esters, Acta Chem. Scan. 24:1590–1596 (1970).*
Rusillo & Clark, The Pharmacology of the Anticholinergic Quaternary Ammonium compound Benzomethamine [N–Diethyllaminoethyl–N'–Methyl–Benzilamide Methobromide (MC 3199)] with a Note on the Tertiary Amine Analogue (MC 3137), J. Pharmacol. Exp. Ther., 11(1):54–62 (1955).*
The Merck Index, 11$^{th}$ ed (1989) Merck and Co. Inc. p. 242 and 802–803.*
Banholzer et al. "preparation of tropanyl . . . " CA 119:28006 (1993).*
Nyberg et al., "Investigations of Diethienylglycolic Esters," *Acta Chem. Scand.,* 24 (1970) No. 5, pp. 1590–1596.
Atkinson et al., *J. Med. Chem.* 1977, vol. 20, No. 12, 1612–17.
Sterling Drug, Inc., *Chem. Abstracts,* vol. 61, No. 1839f (1964).
N–Butylscopolammonium Bromide (Buscopan), *Merck Index,* 10$^{th}$ Edition, pp. 219–220 (1983).
N–Butylscopolammonium Bromide (Buscopan), *Merck Index,* 11$^{th}$ Edition, p. 242 (1989).
Valpin, Goodman & Gilman, *The Pharmacological Basis of Therapeutics,* 6$^{th}$ Edition, p. 130 (MacMillan 1980).

(Continued)

*Primary Examiner*—Celia Chang
(74) *Attorney, Agent, or Firm*—Michael P. Morris; Timothy X. Witkowski; Wendy A. Petka

(57) ABSTRACT

Compounds of the formula

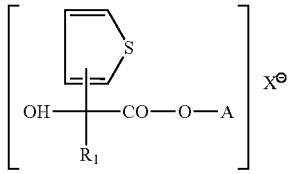

of which, in exemplary compounds, the thienyl group is attached via the 2-position and;

(a) A is 3α-(6β, 7β-epoxy)-tropanyl methobromide and $R_1$ is 2-thienyl;

(b) A is 3α-(6, 7dehydro)-tropanyl methobromide and $R_1$ is 2-thienyl;

(c) A is 3β-tropanyl methobromide and $R_1$ is 2-thienyl; and, (d) A is 3α-(N-isopropyl)-nortropanyl methobromide and $R_1$ is cyclopentyl.

There are anticholinergics. Administered by inhalation, they are useful for the treatment of chronic obstructive bronchitis or slight to moderately severe asthma. Administered by the intravenous or oral routes, they are useful for the treatment of vagally induced sinus bradycardia.

16 Claims, No Drawings

OTHER PUBLICATIONS

Ipratropium Bromide (Atrovent), *Merck Index,* 10$^{th}$ Edition, p. 733 (1983).
Ipratropium Bromide (Atrovent), *Merck Index,* 10$^{th}$ Edition, pp. 802–803 (1989).
Foster et al., "Further New Tropine Derivatives," *Journal of the Chemical Society,* p. 3575–3578 (1957).
Jun. 2, 1992 Examination Report from European Patent Application No. 90117554.7 (EP 418716) and English translation.
Dec. 1, 1992 Reply to Examination Report from European Patent Application No. 90117554.7 (EP 418716) and English translation.
Feb. 5, 1993 Examination Report from European Patent Application No. 90117554.7 (EP 418716) and English translation.
Apr. 23, 1993 Reply to Examination Report from European Patent Application No. 90117554.7 (EP 418716) and English translation.
International Search Report mailed Jan. 10, 1991 from PCT/EP90/01517 (WO 91/04252).

* cited by examiner

ESTERS OF THIENYL CARBOXYLIC ACIDS AND AMINO ALCOHOLS AND THEIR QUATERNIZATION PRODUCTS

Matter enclosed in heavy brackets [ ] appears in the original patent but forms no part of this reissue specification; matter printed in italics indicates the additions made by reissue.

This is a continuation of application Ser. No. 08/254,324, filed on Jun. 6, 1994, now abandoned which is a continuation of application Ser. No. 08/100,822, filed on Aug. 2, 1993, now abandoned, which is a continuation of application Ser. No. 07/838,724, filed on Mar. 13, 1992, now abandoned.

The invention relates to novel thienylcarboxylates of amino alcohols and their quaternary products and to the preparation of the novel compounds and their use as active ingredients in medicaments.

The novel compounds correspond to the formula (I)

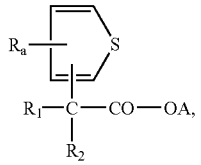

in which

A represents the group (II)

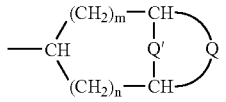

wherein m and n independently of one another denote 1 or 2,

Q represents one of the double-bonding groups

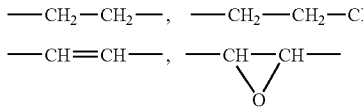

and

Q' represents the group =NR or the group =NRR', wherein

R denotes H or an optionally halogen-substituted or hydroxy-substituted $C_1$-$C_4$-alkyl radical, R' denotes a $C_1$-$C_4$-alkyl radical and R and R' together may also form a $C_4$-$C_6$-alkylene radical, and wherein, in the case of quaternary compounds, one equivalent of an anion ($X^-$)opposes the positive charge of the N atom, $R_1$ represents a thienyl, phenyl, furyl, cyclopentyl or cyclohexyl radical, wherein these radicals may also be methyl-substituted, thienyl and phenyl may also be fluoro-substituted or chloro-substituted, $R_2$ represents hydrogen, OH, $C_1$-$C_4$-alkoxy or $C_1$-$C_4$-alkyl, $R_a$ represents H, F, Cl or $CH_3$ and, if =NR denotes a secondary or tertiary amino group, also the acid addition salts.

In the compounds of formula I, $R_1$ preferably represents thienyl, $R_2$ preferably represents OH. The group —OA preferably has the α-configuration and is derived from, for example scopine, tropine, granatoline or 6,7-dehydrotropine or the corresponding nor-compounds; however, —OA may also have the β-configuration, as in pseudotropine, pseudoscopine.

Corresponding radicals are, for example

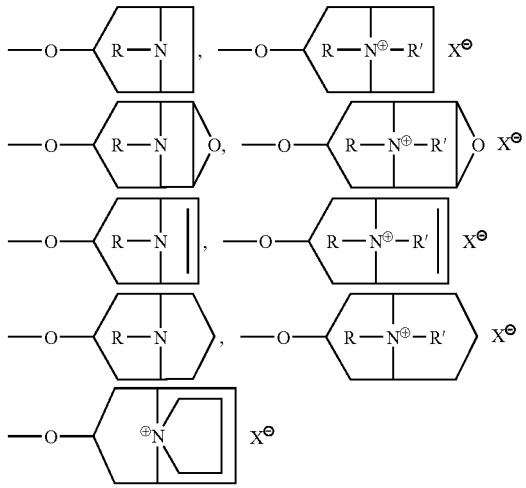

The substituent R is preferably a lower alkyl radical, such as $CH_3$, $C_2H_5$, n-$C_3H_7$, i-$C_3H_7$, R' is preferably $CH_3$. R and R' together are, for example —$(CH_2)_5$—. As halogen substituents for R, F or, as second choice, Cl are suitable.

If R denotes a halogen-substituted or hydroxy-substituted alkyl radical, it is preferably —$CH_2$—$CH_2F$ or —$CH_2$—$CH_2OH$. Accordingly, the group A represents, for example the radicals of scopine, N-ethylnorscopine, N-isopropylnorscopine, tropine, N-isopropylnortropine, 6,7-dehydrotropine, N-β-fluoroethylnortropine, N-isopropyl-6,7-dehydronortropine, N-methylgranatoline or the corresponding quaternary compounds, wherein the anion is preferably $Br^-$ or $CH_3SO_3^-$.

As the acid radical (III)

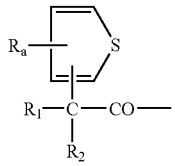

the following are particularly suitable:

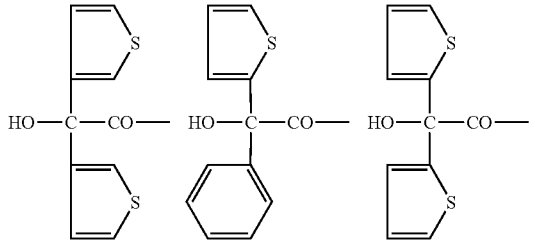

-continued

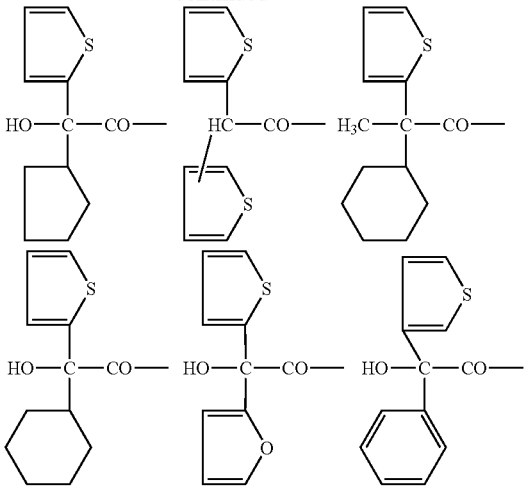

The quaternary compounds are particularly suitable for therapeutic application, whereas the tertiary compounds are important not only as active ingredients but also as intermediate products.

The compounds of the invention are strong anticholinergic agents and have prolonged action. Action lasting at least 24 hours is achieved at inhaled dosages in the μg range. In addition, the toxicity is in the same range as the commercial product Ipratropium bromide, while at the same time the therapeutic effect is stronger.

The novel compounds are suitable, in accordance with their anti-cholinergic nature, for example for the treatment of chronic obstructive bronchitis and (slight to moderately severe) asthma, also for the treatment of vagally induced sinus bradycardia.

Whereas application of the novel active ingredients (in particular the quaternary compounds) by inhalation is mainly recommended for respiratory tract diseases, as a result of which side-effects are largely eliminated, the application for sinus bradycardia is preferably carried out intravenously or orally. It has thus proved to be advantageous that the novel compounds leave the gastro/intestinal motility largely unaffected.

For administration the compounds of the invention are processed using known auxiliaries and/or excipients to give conventional galenic preparations, for example inhalation solutions, suspensions in liquified propellants, preparations containing liposomes or proliposomes, injection solutions, tablets, coated tablets, capsules, inhalation powders for use in conventional inhalation apparatus.

Formulation examples (measures in weight per cent):

| 1. Controlled dosage aerosol | |
|---|---|
| Active ingredient according to the invention | 0.005 |
| Sorbitan trioleate | 0.1 |
| monofluorotrichloromethane and Difluorodichloromethane 2:3 | to 100 |

The suspension is poured into a conventional aerosol container with a dosage valve. 50 μl of suspension are preferably dispensed per actuation. The active ingredient may also be metered in a higher amount if required (for example 0.02 wt. %).

| 2. Tablets | |
|---|---|
| Active ingredient according to the invention | 0.05 |
| Colloidal silicic acid | 0.95 |
| Lactose | 65.00 |
| Potato starch | 28.00 |
| Polyvinylpyrrolidone | 3.00 |
| Na cellulose glycolate | 2.00 |
| Magnesium stearate | 1.00 |

The constituents are processed in conventional manner to give tablets of 200 mg.

The advantageous properties of the novel compounds are shown, for example, in the inhibition of broncholysis in the rabbit (acetylcholine spasms intravenously). After intravenous administration of the novel active ingredients (dosage 3 μg/kg intravenously), the maximum effect occurred after 10 to 40 minutes. After 5 hours the inhibiting effect had still not been reduced to half, that is to say the half effect time is more, in some cases considerably more, than 5 hours, as made clear by the residual effects after 5 hours listed below:

| Compound | Residual effect in % |
|---|---|
| A | 76 |
| B | 76 |
| C | 81 |
| D | 61 |
| E | 68 |
| F | 73 |
| G | 69 |

Compounds of the formula

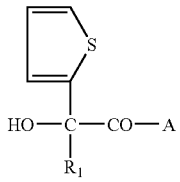

| Compound | A | $R_1$ |
|---|---|---|
| A | 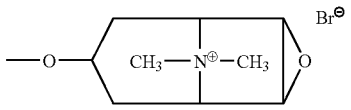 | 2-thienyl |
| B | 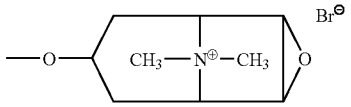 | 3-thienyl |
| D | 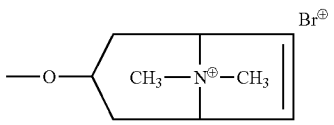 | 2-thienyl |
| E | 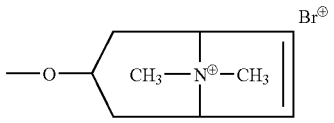 | 3-thienyl |

-continued

F

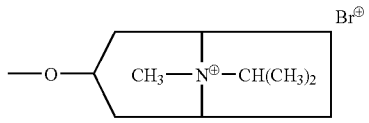

cyclo-pentyl

G

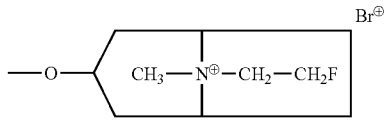

cyclo-pentyl

Compound C

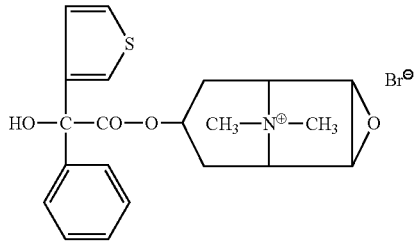

Notes:
1. The compounds in which $R_1$ is not 2-thienyl are racemates.
2. The compounds are 3α-compounds in each case.

Processes known per se are used to prepare the novel compounds.

An ester of the formula

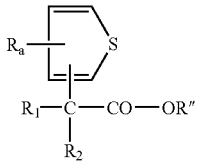

(IV)

wherein R" represents a $C_1$-$C_4$-alkyl radical, preferably a methyl or ethyl radical ($R_1$, $R_2$ and $R_a$ have the above meanings), is preferably transesterified using an amino alcohol of the formula

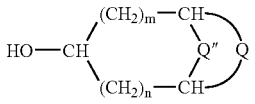

(V)

wherein m, n and Q have the above meanings, Q" represents ═NR or ═NH and the OH group is in the α- or β-position, in the presence of a conventional transesterification catalyst, and the compound obtained is optionally quaternised a) if Q" denotes ═NR (R≠H), using a reactive monofunctionalised derivative Z-($C_1$-$C_4$-alkyl) of a corresponding alkane (Z=leaving group)

or is optionally quaternised b) if Q" denotes ═NH, using a terminally disubstituted alkane Z-($C_4$-$C_6$-alkylene)-Z without isolation of intermediates.

The transesterification is carried out with heat in an organic solvent, for example toluene, xylene, heptane, or in a melt, strong bases such as sodium methylate, sodium ethylate, sodium hydride, metallic sodium, being used as catalyst. Reduced pressure is used to remove the released lower alcohol from the equilibrium, the alcohol is optionally distilled off azeotropically. The transesterification takes place at temperatures which in general do not exceed 95° C. Transesterification often proceeds more favourably in a melt. If required, the free bases may be obtained in a manner known per se from acid addition salts of the tertiary amines using suitable basic compounds. Quaternisation is carried out in suitable solvents, for example acetonitrile or acetonitrile/methylene chloride, preferably at room temperature; a corresponding alkyl halide, for example alkyl bromide, is preferably used in the process as quaternising agent. Transesterification products wherein Q' represents NH are used as starting materials for those compounds in which R and R' together represent a $C_4$-$C_6$-alkylene group. Conversion into the tertiary and then quaternary compound then takes place with the aid of suitable 1,4-dihaloalkanes, 1,5-dihaloalkanes or 1,6-dihaloalkanes without isolation of intermediates.

The starting materials may be obtained analogously to known compounds—in as much as they have not already been described.

EXAMPLES methyl di-(2-thienyl)glycolate from dimethyl oxalate and 2-thienyl magnesium bromide;

ethyl di-(2-thienyl)glycolate from (2-thienyl)glyoxylic acid and 2-thienyl lithium;

ethyl hydroxy-phenyl-(2-thienyl)acetate from methyl phenylglyoxylate and 2-thienyl magnesium bromide or from methyl (2-thienyl)glyoxylate and phenyl magnesium bromide.

Methyl 2-thienylglyoxylate and cyclohexyl or cyclopentyl magnesium bromide may be reacted in a similar manner.

Several processes are also available for the preparation of the amino alcohols.

Pseudoscopine may be obtained in accordance with M. Polonovski et al., Bull. soc. chim. 43, 79 (1928). Pseudotropenol may be removed from the mixture, (fractional crystallisation or distillation) which is obtained, for example in accordance with V. Hayakawa et al., J. Amer. Chem. Soc. 1978, 100(6), 1786 or R. Noyori et al., J. Amer. Chem. Soc. 1974, 96(10), 3336.

The corresponding methyl esters may be prepared in a conventional manner starting from 2-furylglyoxylnitrile or 3-furylglyoxylnitrile via the 2-furylglyoxylic acid or 3-furylglyoxylic acid which can be obtained therefrom. The corresponding glycolates are obtained from these as described using the organometallic derivatives of 2-bromothiophene or 3-bromothiophene. The organometallic compounds which can be obtained from 2-, 3- or 4-halopyridine can be reacted with methyl 2-thienylglyoxylate or methyl 3-thienylglyoxylate to give the corresponding glycolates.

Thienylglycolates, in which the thiophene ring contains fluorine in the 2- or 3-position, are prepared, for example starting from 2-fluorothiophene or 3-fluorothiophene (bromination to give 2-bromo-3-fluorothiophene or 2-bromo-5-fluorothiophene), and after conversion to the corresponding organometallic compounds, reaction with suitable glyoxylates to give the glycolates.

2-Fluorothiophene and 3-fluorothiophene can be reacted analogously to give the corresponding glyoxylates Unterhalt, Arch. Pharm. 322, 839 (1989) which in turn, as already described, may be reacted with, for example 2-thienyl or 3-thienyl derivatives, to give glycolates. Symmetrically substituted di-thienylglycolates can be prepared analogously by selecting suitable components.

A further route is available via a process analogous to the benzoin condensation and benzilic acid rearrangement.

The following examples illustrate the invention without limiting it.

EXAMPLE 1

EXAMPLE 1

Scopine di-(2-thienyl)glycolate 50.87 g (0.2 mole) of methyl di-(2-thienyl)glycolate and 31.04 g (0.2 mole) of scopine are dissolved in 100 ml of absolute toluene and reacted at a bath temperature of 90° C. with addition of 1.65 g (0.071 gram atom) of sodium in several portions. The resulting methanol is distilled off at a reaction mixture temperature of 78°-90° C. under a pressure of 500 mbar. After a reaction time of about 5 hours, the reaction mixture is stirred into a mixture of ice and hydrochloric acid. The acid phase is separated off, rendered alkaline using sodium carbonate and the free base is extracted using methylene chloride. After drying over sodium sulphate, the methylene chloride is distilled off under reduced pressure and the residue is recrystallised from acetonitrile; beige-coloured crystals (from acetonitrile).

m.p. 149°-50° C.

Yield: 33.79 g (44.7% of theoretical).

EXAMPLE 2

Scopine di-(2-thienyl)glycolate 12.72 g (0.05 mole) of methyl di-(2-thienyl)glycolate and 7.76 g (0.05 mole) of scopine are melted in a heating bath at 70° C. under a water jet vacuum. 2.70 g (0.05 mole) of sodium methylate are introduced into this melt and heated for 1 hour in a heating bath at 70° C. under a water jet vacuum and subsequently for a further hour in a heating bath at 90° C. The solidified melt is taken up in a mixture of 100 ml of water and 100 ml of methylene chloride while monitoring the temperature, and the methylene chloride phase is extracted several times using water. The methylene chloride phase is extracted using the corresponding amount of dilute hydrochloric acid. The scopine di-(2-thienyl)glycolate is extracted from the combined aqueous phases using methylene chloride after adding the corresponding amount of sodium carbonate and dried over sodium sulphate. The hydrochloride is prepared from the dried methylene chloride solution in a conventional manner. The crystals are filtered off under suction, washed using acetone and dried under reduced pressure at 35° C. Pale yellow crystals (from methanol), m.p. 238°-41° C. (decomposition);

Yield: 10.99 g (53.1% of theoretical).

The hydrochloride may be converted to the base in a conventional manner.

EXAMPLE 3

Scopine di-(2-thienyl)glycolate 38.15 g (0.15 mole) of methyl di-(2-thienyl)glycolate and 23.28 g (0.15 mole) of scopine are mixed, 0.34 g (0.015 gram atom) of sodium is added and the mixture is melted in a heating bath at 90° C. under a water jet vacuum. The reaction lasts 2.5 hours. 100 ml of absolute toluene are then added and the mixture is stirred at a heating bath temperature of 90° C. until a solution is produced. The reaction solution is cooled to room temperature and stirred into a mixture of ice and hydrochloric acid cooled using ice. The hydrochloride of the basic ester crystallising out is filtered off under suction and washed using a small amount of water and a large amount of diethyl ether. The filtrate phases are separated off and the aqueous phase is extracted using diethyl ether. The hydrochloride filtered off under suction is suspended in the (acid) aqueous phase and converted to the base while monitoring the temperature and adding the corresponding amount of sodium carbonate; the base is extracted using methylene chloride. The combined methylene chloride phases are dried over sodium sulphate. After distilling off the methylene chloride, crystals remain which are purified over active charcoal and recrystallised from acetonitrile. Pale yellow crystals (from acetonitrile), m.p. 148°-49° C.;

Yield: 39.71 g (70.1% of theoretical).

TABLE I

Compounds of the formula

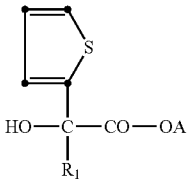

| No. | A | $R_1$ | Base | M.p. [° C.] Hydrochloride |
|---|---|---|---|---|
| 1 | 3α-(6β,7β-epoxy)-tropanyl | 2-thienyl | 149-50 | 238-41 |
| 2 | 3α-tropanyl | 2-thienyl | 167-8 | 253 |
| 3 | 3α-(6,7-dehydro)-tropanyl | 2-thienyl | 164-5 | |
| 4 | 3α-(N-β-fluoroethyl)-nortropanyl | 2-thienyl | | 236 |
| 5 | 3α-(N-isopropyl)-granatanyl | 2-thienyl | | 232 |
| 6 | 3α-(N-isopropyl)-nortropanyl | 2-thienyl | | 256 |
| 7 | 3α-(6β,7β-epoxy)-N-isopropyl-nortropanyl | 2-thienyl | | 206 |
| 8 | 3α-(6β,7β-epoxy)-N-ethyl nortropanyl | 2-thienyl | | 212-3 |
| 9 | 3α-(N-ethyl)-nortropanyl | 2-thienyl | | 256-7 |
| 10 | 3α-(N-N-methyl)-granatanyl | 2-thienyl | | 241 |
| 11 | 3α-(6β,7β-epoxy)-N-β fluoroethylnortropanyl | 2-thienyl | | 188-90 |
| 12 | 3α-(6β,7β-epoxy)-N-n propylnortropanyl | 2-thienyl | | 104-6 |
| 13 | 3α-(6β,7β-epoxy)-N-n butylnortropanyl | 2-thienyl | | 225-7 |
| 14 | 3α-(6β,7β-epoxy)-tropanyl | phenyl | | 246-7 |
| 15 | 3α-tropanyl | phenyl | | 243-4 |
| 16 | 3α-(N-β-fluoroethyl)-nortropanyl | phenyl | | 219-20 |
| 17 | 3α-(6,7-dehydro)-tropanyl | phenyl | | 181-3 |
| 18 | 3α-(N-ethyl)-nortropanyl | phenyl | | 231-2 |
| 19 | 3α-(N-isopropyl)-nortropanyl | phenyl | | 246-7 |
| 20 | 3α-tropanyl | cyclo-hexyl | | 260 |
| 21 | 3α-(N-β-fluoroethyl)-nortropanyl | cyclo-hexyl | | 203-4 |
| 22 | 3α-(6β,7β-epoxy)-tropanyl | cyclo-pentyl | | 237 |
| 23 | 3α-tropanyl | cyclo-pentyl | | 260 |
| 24 | 3α-(N-β-fluoroethyl)-nortropanyl | cyclo-pentyl | | 182-3 |
| 25 | 3α-(N-ethyl)-nortropanyl | cyclo-pentyl | | 227-8 |
| 26 | 3α-(N-isopropyl)-nortropanyl | cyclo-pentyl | | 174-5 |
| 27 | 3α-(6β,7β-epoxy)-tropanyl | 2-thienyl | | 240-2 |

TABLE I-continued

Compounds of the formula

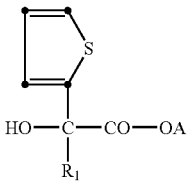

| No. | A | $R_1$ | Base | M.p. [° C.] Hydro-chloride |
|---|---|---|---|---|
| 28 | 3β-tropanyl | 2-thienyl | | 217-9 |
| 29 | 3β-(6,7-dehydro)-tropanyl | 2-thienyl | | 233-5 |
| 30 | 3α-(6,7-dehydro)-trapanyl | 3-thienyl | | 247-8 |
| 31 | 3α-(6β,7β-epoxy)-tropanyl | 3-thienyl | | 242-3 |
| 32 | 3α-(6β,7β-epoxy)-tropanyl | 2-furyl | | |
| 33 | 3α-(6,7-dehydro)-tropanyl | 2-furyl | | |
| 34 | 3α-tropanyl | 2-furyl | | |
| 35 | 3α-tropanyl | 2-pyridyl | | |
| 36 | 3α-(6β,7β-epoxy)-tropanyl | 2-pyridyl | | |
| 37 | 3α-(6,7-dehydro)-tropanyl | 2-pyridyl | | |
| 38 | 3α-tropanyl | 3-thienyl | | |
| 39 | 3α-(6,7-dehydro)-tropanyl | cyclo-pentyl | | |
| 40 | 3α-(6β,7β-epoxy)-tropanyl | cyclo-hexyl | | |
| 41 | 3α-(6,7-dehydro)-tropanyl | cyclo-hexyl | | |

Note:
All hydrochlorides melt with decomposition.

EXAMPLE 4

Scopine di-(2-thienyl)glycolate methobromide 10.0 g (0.0265 mole) of scopine di-(2-thienyl)glycolate are dissolved in a mixture comprising 20 ml of anhydrous methylene chloride and 30 ml of anhydrous acetonitrile and treated with 12.8 g (0.1325 mole) of methyl bromide (as 50% strength solution in anhydrous acetonitrile), and the reaction mixture is allowed to stand for 24 hours at room temperature in a tightly sealed reaction vessel. Crystals are precipitated during this time. They are filtered off under suction, washed using methylene chloride and dried at 35° C. under reduced pressure. White crystals (from methanol/acetone), m.p. 217°-8° C. (decomposition) after drying at 111° C. under reduced pressure.

TABLE II

Quaternary compounds of the formula

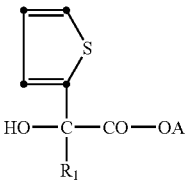

| No. | A | $R_1$ | M.p. [° C.] |
|---|---|---|---|
| 1 | 3α-(6β,7β-epoxy)-tropanyl methobromide | 2-thienyl | 217-18 |
| 2 | 3α-tropanyl methobromide | 2-thienyl | 263-64 |

TABLE II-continued

Quaternary compounds of the formula

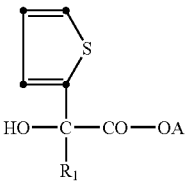

| No. | A | $R_1$ | M.p. [° C.] |
|---|---|---|---|
| 3 | 3α-(6,7-dehydro)-tropanyl methobromide | 2-thienyl | 191-92 |
| 4 | 3α-(N-β-fluoroethyl)-nortropanylmethobromide | 2-thienyl | 242-43 |
| 5 | 3α-tropanyl-β-fluoroethobromide | 2-thienyl | 214-15 |
| 6 | 3α-(N-isopropyl)-granatanyl methobromide | 2-thienyl | 229-30 |
| 7 | 3α-(N-isopropyl)-nortropanylmethobromide | 2-thienyl | 245-46 |
| 8 | 3α-(6β,7β-epoxy)-N-isopropyl-nortropanyl methobromide | 2-thienyl | 223-24 |
| 9 | 3α-(6β,7β-epoxy)-N-ethylnortropanyl methobromide | 2-thienyl | 215-16 |
| 10 | 3α-(N-ethyl)-nortropanyl methobromide | 2-thienyl | 260-61 |
| 11 | 3α-(N-methyl)-granatanyl methobromide | 2-thienyl | 246-47 |
| 12 | 3α-(6β,7β-epoxy)-N-fluoroethyl-nortropanyl methobromide | 2-thienyl | 182-83 |
| 13 | 3α-(6β,7β-epoxy)-N-n-propylnortropanyl methobromide | 2-thienyl | 209-10 |
| 14 | 3α-tropanyl-β-hydroxyethobromide | 2-thienyl | 231-32 |
| 15 | 3α-(6β,7β-epoxy)-tropanyl ethobromide | phenyl | 217-18 |
| 16 | 3α-tropanyl methobromide | phenyl | 273-74 |
| 17 | 3α-(N-β-fluoroethyl)-nortrapanylmethobromide | phenyl | |
| 18 | 3α-(6,7-dehydro)-tropanyl methobromide | phenyl | 110-71 |
| 19 | 3α-(N-ethyl)-nortropanyl methobromide | phenyl | 249-50 |
| 20 | 3α-(N-isopropyl)-nortropanyl methobromide | phenyl | 259-60 |
| 21 | 3α-tropanyl ethobromide | phenyl | 248-49 |
| 22 | 3α-(N-ethyl)-nortropanyl ethobromide | phenyl | 244-45 |
| 23 | 3α-(6β,7β-epoxy)-tropanyl ethobromide | phenyl | 226 |
| 24 | 3α-tropanyl-β-fluoroethobromide | phenyl | 241 |
| 25 | 3α-tropanyl methobromide | cyclohexyl | 278 |
| 26 | 3α-(N-β-fluoroethyl)-nortropanyl methobromide | cyclohexyl | 198 |
| 27 | 3α-tropanyl-β-fluoroethobromide | cyclohexyl | 233-34 |
| 28 | 3α-tropanyl methobromide | cyclopentyl | 260 |
| 29 | 3α-tropanyl ethobromide | cyclopentyl | 235-36 |
| 30 | 3α-(N-ethyl)-nortropanyl methobromide | cyclopentyl | 251-52 |
| 31 | 3α-(N-isopropyl)-nortropanyl-methobromide | cyclopentyl | 244-45 |
| 32 | 3α-tropanyl-β-fluoroethobromide | cyclopentyl | 189-90 |
| 33 | 3α-(N-β-fluoroethyl)-nortropanyl-methobromide | cyclopentyl | 226-27 |
| 34 | 3α-(6,7-dehydro)-tropanyl metho-methanesulphonate | 2-thienyl | 225-6 |
| 35 | 3α-(6β,7β-epoxy)-tropanyl methobromide | 2-thienyl | 218-20 |

TABLE II-continued

Quaternary compounds of the formula

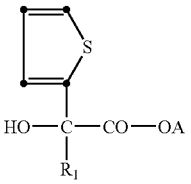

| No. | A | $R_1$ | M.p. [° C.] |
|---|---|---|---|
| 36 | 3α-tropanyl methobromide | 2-thienyl | 243-4 |
| 37 | 3α-(6,7-dehydro)-tropanyl methobromide | 2-thienyl | 211-4 |
| 38 | 3α-(6,7-dehydro)-tropanyl methobromide | 3-thienyl | 182-3* |
| 39 | 3α-(6β,7β-epoxy)-tropanyl methobromide | 3-thienyl | 217-8 |
| 40 | (+) enantiomer of No. 1 | | |
| 41 | (−) enantiomer of No. 1 | | |
| 42 | 3α-(6β,7β-epoxy)-tropanyl methobromide | 2-furyl | |
| 43 | 3α-(6,7-dehydro)-tropanyl methobromide | 2-furyl | |
| 44 | 3α-tropanyl methobromide | 2-furyl | |
| 45 | 3α-(6β,7β-epoxy)-tropanyl methobromide | 2-pyridyl | |
| 46 | 3α-(6,7-dehydro)-tropanyl methobromide | 2-pyridyl | |
| 47 | 3α-tropanyl methobromide | 2-pyridyl | |
| 48 | 3α-tropanyl methobromide | 3-thienyl | |
| 49 | 3α-(6,7-dehydro)-tropanyl methobromide | cyclopentyl | |
| 50 | 3α-(6β,7β-epoxy)-tropanyl methobromide | cyclohexyl | |
| 51 | 3α-(6,7-dehydro)-tropanyl methobromide | cyclohexyl | |
| 52 | 3α-(6β,7β-epoxy)-tropanyl methobromide | cyclohexyl | |

*contains crystalline methanol

Note:

All compounds in the table melt with decomposition.

TABLE III

Compounds of the formula

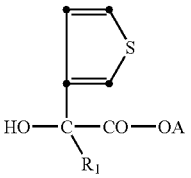

| No. | A | $R_1$ | M.p. [° C.] Hydrochloride |
|---|---|---|---|
| 1 | 3α-(6β,7β-epoxy)-tropanyl | phenyl | 246-7 |
| 2 | 3α-(6,7-dehydro)-tropanyl | phenyl | 261-2 |
| 3 | 3α-(6β,7β-epoxy)-tropanyl | 3-thienyl | |
| 4 | 3α-(6,7-dehydro)-tropanyl | 3-thienyl | |
| 5 | 3α-tropanyl | 3-thienyl | |
| 6 | 3α-(N-methyl)-granatanyl | 3-thienyl | |

TABLE IV

Compounds of the formula

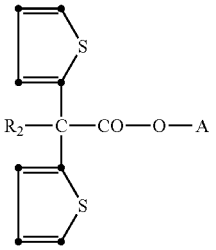

| No. | A | $R_2$ | M.p. [° C.] Hydrochloride |
|---|---|---|---|
| 1 | 3α-(6β,7β-epoxy)-tropanyl | H | |
| 2 | 3α-(6,7-dehydro)-tropanyl | H | |
| 3 | 3α-(6β,7β-epoxy)-tropanyl | methyl | |
| 4 | 3α-(6,7-dehydro)-tropanyl | methyl | 210-2.5 |
| 5 | 3α-(6β,7β-epoxy)-tropanyl | methoxy | |
| 6 | 3α-(6,7-dehydro)-tropanyl | methoxy | |

TABLE V

Compounds of the formula

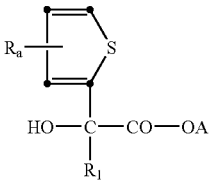

| No. | A | $R_2$ | $R_a$ | M.p. [° C.] |
|---|---|---|---|---|
| 1 | 3α-(6β,7β-epoxy)-tropanyl | 2-thienyl | 5-methyl | |
| 2 | 3α-(6,7-dehydro)-tropanyl | 2-thienyl | 5-methyl | |
| 3 | 3α-tropanyl | 2-thienyl | 5-methyl | |
| 4 | 3α-(6β,7β-epoxy)-tropanyl | 2-(5-methyl)-thienyl | 5-methyl | |
| 5 | 3α-(6,7-dehydro)-tropanyl | 2-(5-methyl)-thienyl | 5-methyl | |
| 6 | 3α-tropanyl thienyl | 2-(5-methyl)- | 5-methyl | |
| 7 | 3α-(6β,7β-epoxy)-tropanyl | 2-thienyl | 5-fluoro | |
| 8 | 3α-(6,7-dehydro)-tropanyl | 2-thienyl | 5-fluoro | |
| 9 | 3α-tropanyl | 2-thienyl | 5-fluoro | |
| 10 | 3α-(6β,7β-epoxy)-tropanyl | 2-(5-fluoro)-thienyl | 5-fluoro | |
| 11 | 3α-(6,7-dehydro)-tropanyl | 2-(5-fluoro)-thienyl | 5-fluoro | |
| 12 | 3α-tropanyl | 2-(5-fluoro)-thienyl | 5-fluoro | |

TABLE VI

Compounds of the formula

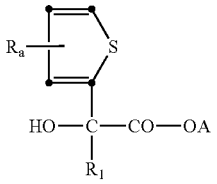

| No. | A | $R_1$ | $R_a$ | M.p. [° C.] |
|---|---|---|---|---|
| 1 | 3α-(6β,7β-epoxy)-tropanyl methobromide | 2-thienyl | 5-methyl | |
| 2 | 3α-(6,7-dehydro)-tropanyl methobromide | 2-thienyl | 5-methyl | |
| 3 | 3α-tropanyl-methobromide | 2-thienyl | 5-methyl | |
| 4 | 3α-(6β,7β-epoxy)-tropanyl methobromide | 2-(5-methyl)-thienyl | 5-methyl | |
| 5 | 3α-(6,7-dehydro)-tropanyl methobromide | 2-(5-methyl)-thienyl | 5-methyl | |
| 6 | 3α-tropanyl methobromide | 2-(5-methyl)-thienyl | 5-methyl | |
| 7 | 3α-(6β,7β-epoxy)-tropanyl methobromide | 2-thienyl | 5-fluoro | |
| 8 | a-(6,7-dehydro)-tropanyl methobromide | 2-thienyl | 5-fluoro | |
| 9 | 3α-tropanyl methobromide | 2-thienyl | 5-fluoro | |
| 10 | 3α-(6β,7β-epoxy)-tropanyl methobromide | 2-(5-fluoro)-thienyl | 5-fluoro | |
| 11 | 3α-(6,7-dehydro)-tropanyl methobromide | 2-(5-fluoro)-thienyl | 5-fluoro | |
| 12 | 3α-tropanyl methobromide | 2-(5-fluoro)-thienyl | 5-fluoro | |

TABLE VII

Compounds of the formula

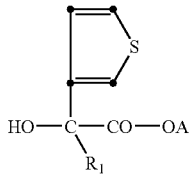

| No. | A | $R_1$ | M.p. [° C.] |
|---|---|---|---|
| 1 | 3α-(6β,7β-epoxy)-tropanyl methobromide | phenyl | 211-2 |
| 2 | 3α-(6,7-dehydro)-tropanyl methobromide | phenyl | 158-60* |
| 3 | 3α-(6β,7β-epoxy)-tropanyl methobromide | 3-thienyl | |
| 4 | 3α-(6,7-dehydro)-tropanyl methobromide | 3-thienyl | |
| 5 | 3α-tropanyl methobromide | 3-thienyl | |
| 6 | 3α-(N-methyl)-granatanyl methobromide | 3-thienyl | |

*(with crystalline methanol)

TABLE VIII

Quaternary compounds of the formula

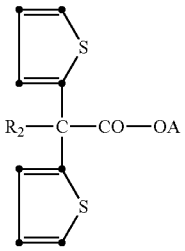

| No. | A | $R_2$ | M.p. [° C.] |
|---|---|---|---|
| 1 | 3α-(6β,7β-epoxy)-tropanyl methobromide | H | |
| 2 | 3α-(6,7-dehydro)-tropanyl methobromide | H | |
| 3 | 3α-(6β,7β-epoxy)-tropanyl methobromide | methyl | |
| 4 | 3α-(6,7-dehydro)-tropanyl methobromide | methyl | 206-8 |
| 5 | 3α-tropanyl methobromide | methoxy | |
| 6 | 3α-(N-methyl)-tropanyl methobromide | methoxy | |

We claim:

1. A compound of the formula

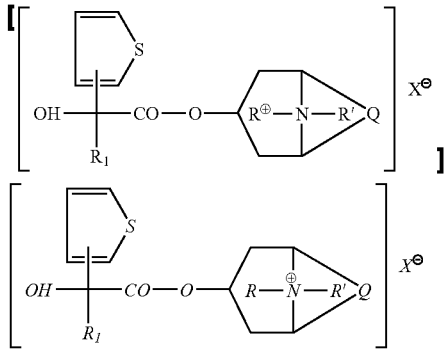

wherein

Q is a group of the formula [$—CH_2—CH_2—$,] —CH═CH— or

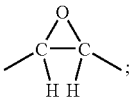

R and R' are each independently $C_1$-$C_4$-alkyl;

$R_1$ is thienyl, phenyl, cyclopentyl or cyclohexyl; and, $X^-$ is a physiologically acceptable anion.

2. A compound in accordance with claim 1, of the formula

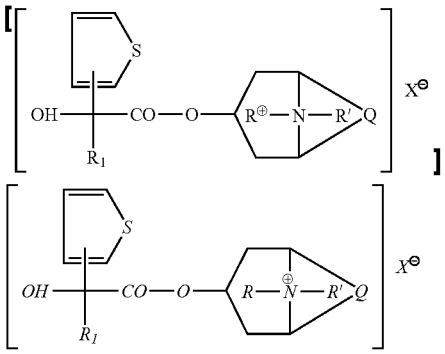

wherein

R is $CH_3$, $C_2H_5$, n-$C_3H_7$, or i-$C_3H_7$;

R' is $CH_3$; and $R_1$, Q and $X^-$ are as defined in claim 1.

3. A compound in accordance with claim 2 wherein $R_1$ is thienyl.

4. A compound in accordance with claim 2 wherein $X^-$ is $Br^-$ or [$CH_3SO_3$] $CH_3SO_3^-$.

5. A compound of the formula

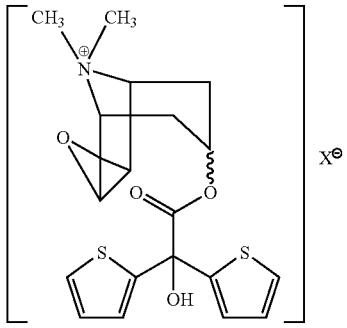

wherein $X^-$ is a physiologically acceptable anion.

6. A compound of the formula

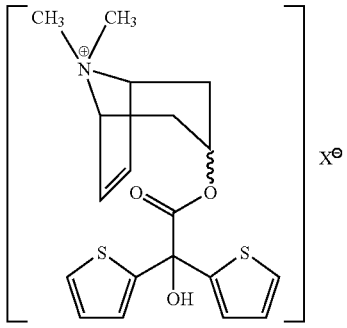

wherein $X^-$ is a physiologically acceptable onion.

7. A compound of the formula

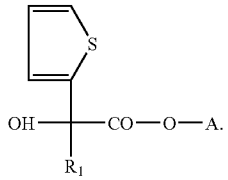

8. A compound of the formula

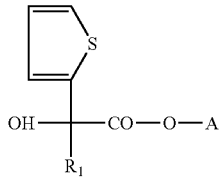

wherein $R_1$ is 2-thienyl and A is 3α-(6,7-dehydro)-tropanyl methobromide.

[9. A compound of the formula

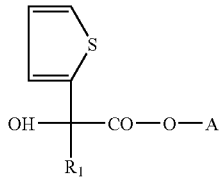

wherein $R_1$ is 2-thienyl and A is 3β-tropanyl methobromide.]

[10. A compound of the formula

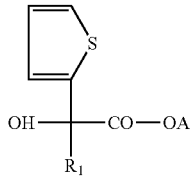

wherein $R_1$ is cyclopentyl and A is 3α-(N-isopropyl)-nortropanyl methobromide.]

11. A method for treating chronic obstructive bronchitis which comprises administering, by inhalation, to a subject suffering from the same, a therapeutic amount of a compound in accordance with claims 1, 2, 3, 4, 6, 7, *or* 8[, 9, 10].

[12. A method for treating slight to moderately severe asthma which comprises administering, by inhalation, to a subject suffering from the same, a therapeutic amount of a compound in accordance with claims 1, 2, 3, 4, 6, 7, 8, 9, 10.]

13. A method for treating vagally induced sinus bradycardia which comprises administering, by the intravenous or oral routes, to a subject suffering from the same, a therapeutic amount of a compound in accordance with claims 1, 2, 3, 4, 6, 7, *or* 8[, 9, 10].

14. A pharmaceutical composition, for administration by inhalation, suitable for the treatment of chronic obstructive bronchitis [or slight to moderately severe asthma], which comprises a compound in accordance with claims 1, 2, 3, 4, 6, 7, *or* 8[, 9, 10].

15. A pharmaceutical composition for oral administration, suitable for the treatment of vagally induced sinus bradycardia, which comprises a compound in accordance with claims 1, 2, 3, 4, 6, 7, *or* 8[, 9, 10].

16. A pharmaceutical composition, for intravenous administration, suitable for the treatment of vagally induced sinus bradycardia, which comprises a compound in accordance with claims 1, 2, 3, 4, 6, 7, *or* 8[, 9, 10].

*17. A method for treating chronic obstructive bronchitis which comprises administering, by inhalation, to a subject suffering from the same, a therapeutic amount of a compound in accordance with claim 5.*

*18. A pharmaceutical composition, for administration by inhalation, suitable for the treatment of chronic obstructive bronchitis, which comprises a compound in accordance with claim 5.*

*19. A pharmaceutical composition, for administration by inhalation, suitable for the treatment of chronic obstructive bronchitis, comprising an inhalation powder comprising a compound in accordance with claim 5.*

* * * * *

UNITED STATES PATENT AND TRADEMARK OFFICE

CERTIFICATE OF CORRECTION

PATENT NO. : RE 39,820 E
APPLICATION NO. : 11/254213
DATED : September 4, 2007
INVENTOR(S) : Banholzer et al.

It is certified that error appears in the above-identified patent and that said Letters Patent is hereby corrected as shown below:

Column 15, line 29, change "$[CH_3SO_3]CH_3SO_3$-" to --$[CH_3SO_3]\ CH_3SO_3^-$ --

Column 15, line 67, change "onion." to --anion.--

Column 16, line 10, after the figure, insert --wherein $R_1$ is 2-thienyl and A is 3α-(6β, 7β-epoxy)-tropanyl methobromide.--

Column 16, line 50, change "1, 2, 3, 4, 6, 7, or 8 [,9, 10]" to --1, 2, 3, 4, 6, 7, or 8 [, 9 or 10]--

Column 16, line 54, change "1, 2, 3, 4, 6, 7, 8, 9, 10" to --1, 2, 3, 4, 6, 7, 8, 9 or 10--

Column 16, line 59, change "1, 2, 3, 4, 6, 7, or 8[, 9, 10]" to --1, 2, 3, 4, 6, 7, or 8 [, 9 or 10]--

Column 16, line 64, change "1, 2, 3, 4, 6, 7, or 8[, 9, 10]" to --1, 2, 3, 4, 6, 7, or 8 [, 9 or 10]--

Column 17, line 2, change "1, 2, 3, 4, 6, 7, or 8[, 9, 10]" to --1, 2, 3, 4, 6, 7, or 8 [, 9 or 10]--

Column 17, line 6, change "1, 2, 3, 4, 6, 7, or 8[, 9, 10]" to --1, 2, 3, 4, 6, 7, or 8 [, 9 or 10]--

Signed and Sealed this

Eighth Day of January, 2008

JON W. DUDAS
*Director of the United States Patent and Trademark Office*